US011244308B1

(12) United States Patent
Stankiewicz et al.

(10) Patent No.: US 11,244,308 B1
(45) Date of Patent: Feb. 8, 2022

(54) RECORDS OF A TANGIBLE PRODUCT IN BLOCKCHAIN

(71) Applicants: Brian Stankiewicz, St. Paul, MN (US); Nicholas Brian Stankiewicz, St. Paul, MN (US)

(72) Inventors: Brian Stankiewicz, St. Paul, MN (US); Nicholas Brian Stankiewicz, St. Paul, MN (US)

( * ) Notice: Subject to any disclaimer, the term of this patent is extended or adjusted under 35 U.S.C. 154(b) by 0 days.

(21) Appl. No.: 17/139,691

(22) Filed: Dec. 31, 2020

(51) Int. Cl.
| *G06Q 20/00* | (2012.01) |
| *G06Q 20/36* | (2012.01) |
| *H04L 9/06* | (2006.01) |
| *G06Q 20/40* | (2012.01) |
| *G06Q 20/06* | (2012.01) |
| *G06K 19/06* | (2006.01) |
| *G16H 20/00* | (2018.01) |
| *G06Q 30/06* | (2012.01) |
| *G06K 19/077* | (2006.01) |

(52) U.S. Cl.
CPC ... *G06Q 20/3678* (2013.01); *G06K 19/06159* (2013.01); *G06Q 20/0658* (2013.01); *G06Q 20/405* (2013.01); *G06Q 30/0635* (2013.01); *G16H 20/00* (2018.01); *H04L 9/0618* (2013.01); *G06K 19/06037* (2013.01); *G06K 19/07758* (2013.01); *H04L 2209/38* (2013.01)

(58) Field of Classification Search
CPC .. G06Q 20/3678; G06Q 20/405; G16H 20/20; G06K 19/06159
USPC .......................................................... 705/69
See application file for complete search history.

(56) References Cited

U.S. PATENT DOCUMENTS

| 5,974,150 A | 10/1999 | Kaish et al. |
| 6,025,200 A | 2/2000 | Kaish et al. |
| 7,089,420 B1 | 8/2006 | Durst et al. |
| 7,773,749 B1 | 8/2010 | Durst et al. |
| 8,171,567 B1 | 5/2012 | Fraser et al. |
| 8,737,609 B1 | 5/2014 | Durst et al. |
| 10,176,481 B2 | 1/2019 | Aljawhari |
| 10,922,757 B2* | 2/2021 | Hu ........................ G06F 16/245 |
| 2016/0210547 A1* | 7/2016 | Dekeyser ......... G06K 19/07758 |
| 2018/0117446 A1* | 5/2018 | Tran ..................... A42B 3/0433 |
| 2018/0130034 A1 | 5/2018 | Taylor et al. |
| 2018/0165588 A1* | 6/2018 | Saxena ................. G06Q 20/02 |

(Continued)

OTHER PUBLICATIONS

International Search Report for related Patent Application No. PCT/US2020/057711 dated Mar. 29, 2021.

*Primary Examiner* — Ahshik Kim
(74) *Attorney, Agent, or Firm* — Dicke, Billig & Czaja, PLLC

(57) ABSTRACT

Generating records of a tangible object in blockchain may be performed by a non-transitory computer-readable storage medium comprising instructions. The instructions, when executed cause a computing device to associate a unique physical tag with a tag identifier. The unique physical tag includes a substrate having a plurality of optically readable indicia disposed at random positions and having a fixed positional relationship within the substrate. The instructions, when executed cause the computing device to associate the tangible object with the unique physical tag including the tag identifier, by generating a record of the tangible object as a block in a blockchain uniquely associated with the tag identifier, where the blockchain is managed by one or more devices on a decentralized network.

18 Claims, 7 Drawing Sheets

(56) References Cited

U.S. PATENT DOCUMENTS

| | | | |
|---|---|---|---|
| 2018/0343114 A1* | 11/2018 | Ben-Ari | ............... H04L 9/06 |
| 2019/0213371 A1 | 7/2019 | Endress et al. | |
| 2019/0213462 A1 | 7/2019 | McDonald et al. | |
| 2019/0251078 A1* | 8/2019 | Yan | ............... G06F 16/27 |
| 2020/0118094 A1 | 4/2020 | Haldenby et al. | |
| 2020/0320220 A1* | 10/2020 | Beno | ............... G16H 10/60 |
| 2020/0357004 A1* | 11/2020 | Rueda Galán | ......... G06Q 30/01 |

\* cited by examiner

RECORDS OF A TANGIBLE PRODUCT IN BLOCKCHAIN

BACKGROUND

This invention describes a method and process for creating provenance of an object using physical tags that are associated with addresses and processes in a blockchain. Blockchain systems have been proposed for a variety of application scenarios, including applications in the financial industry, healthcare, emerging markets, and so forth. An early example of a blockchain was a cryptocurrency. The cryptocurrency was generated when new blocks were created on the blockchain to confirm transactions of the cryptocurrency. The new blocks may confirm the transfer of cryptocurrency generated in earlier blocks. The blocks on the blockchain were cryptographically proofed and linked to earlier blocks and served as an immutable record of the events in a trustless decentralized peer-to-peer network. For example, a cryptocurrency (e.g., bitcoin) is represented as a chain of events that transfers ownership from one party to another party on a blockchain without an intermediary. Each event transferring ownership from one party to another is cryptographically proofed by including the public key of the new owner. Also, each event is digitally signed with the current owner's private key.

A new block in a blockchain is filled with cryptographically proofed events until the block reaches a specified size limit. A hash digest of all the event identifiers within the block and the block header of the previous block are added as the first event in the block. Each block of events may be secured by participants on a peer-to-peer network. Participants collect new events to create the new block, validate the events on the new block by verifying the cryptographic proofs of each event to verify the cryptocurrency was not spent earlier, and finally solve a mathematical puzzle based on the hash digest, previous block header and a random number.

BRIEF DESCRIPTION OF THE DRAWINGS

FIG. 3 illustrates an example transaction between a platform operator and a trading card company (TCC).

FIG. 4 illustrates an example method of assigning and paying royalties using blockchain, as described herein.

FIG. 5 illustrates an example method of a CountBase feature, consistent with the present disclosure.

FIG. 6 illustrates an example computing device for identifying ownership of an item using the blockchain method described herein.

FIG. 7 illustrates a magnified view 703 of a unique physical tag 705 including a substrate 709 having a plurality of optically readable indicia 707-1, 707-2, . . . 707-N disposed at random positions and having a fixed positional relationship within the substrate 709, consistent with the present disclosure.

DETAILED DESCRIPTION

Figure 1:
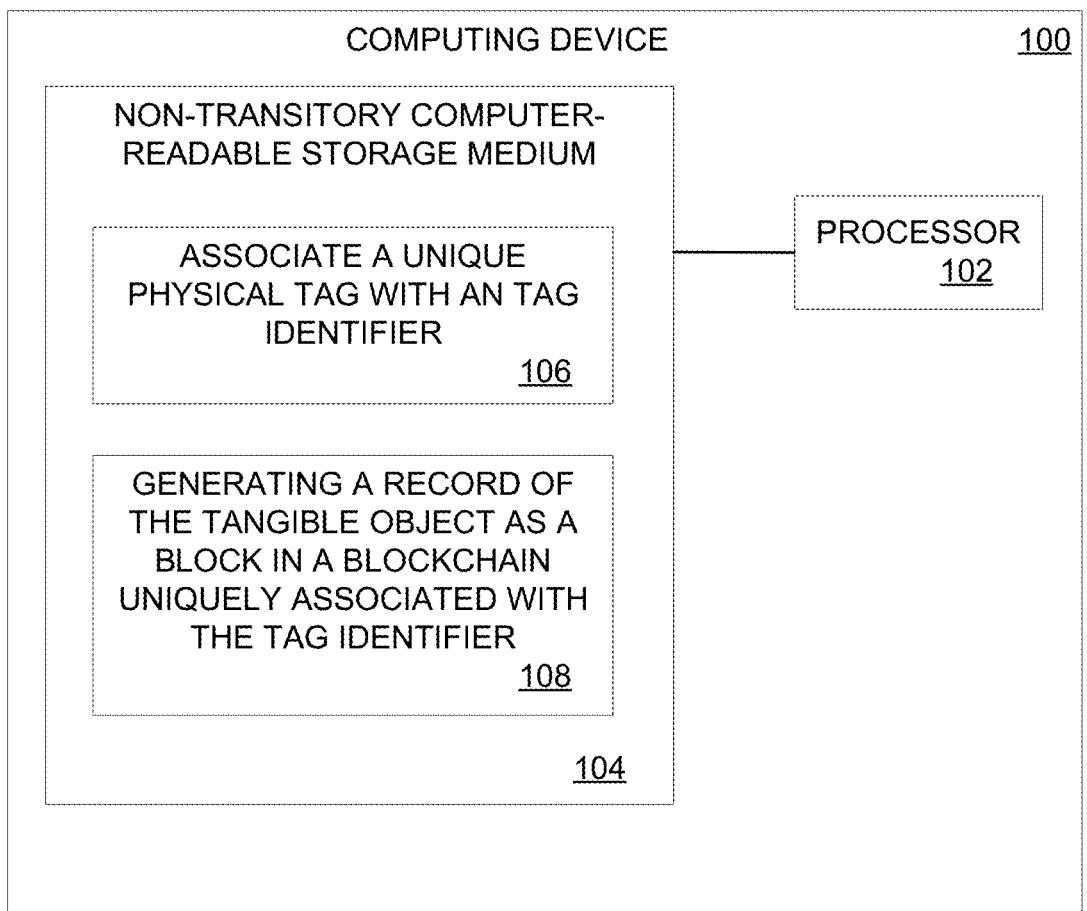
FIG. 1 illustrates an example block diagram of a computing device including instructions to generate records of a tangible object in blockchain, consistent with the present disclosure.

In the following detailed description, reference is made to the accompanying drawings which form a part hereof, and in which is shown by way of illustration specific examples in which the disclosure may be practiced. It is to be understood that other examples may be utilized and structural or logical changes may be made without departing from the scope of the present disclosure. The following detailed description, therefore, is not to be taken in a limiting sense, and the scope of the present disclosure is defined by the appended claims. It is to be understood that features of the various examples described herein may be combined, in part or whole, with each other, unless specifically noted otherwise.

For physical objects, such as televisions, handbags, sports memorabilia and other non-limiting examples, consumers currently have no objective way of determining an object's provenance. An object provenance would include the original manufacturer of the object, the chain of custody including the current owner of the object among other non-limiting information about the object. These provenance factors (e.g., original manufacturer, interim and current ownership) can have a significant impact on the value of the object and whether the object can be legally exchanged. Currently, consumers have to rely on the reputation of the seller to infer the authenticity of the object and the current owner. For some objects, experts can scrutinize an object to determine if it is authentic by looking for typical signs of a counterfeit.

Manufacturers also cannot prove that an object was both manufactured and originally owned by the manufacturer. Counterfeiting is a significant problem to manufacturers and they currently spend a significant amount of resources to find and identify objects not created by them but are packaged as if they were manufactured by them (i.e., counterfeited). This includes scrutinizing items in shipping containers, investigating vendors and retail establishments. Counterfeiting can be done either by a manufacturing company trying to copy the materials and processes used by the manufacturer to create an object that is difficult to distinguish from an authentic object. Oftentimes scrutiny by an expert can distinguish between a counterfeit and an authentic object in this case. However, counterfeiting becomes even more challenging when a parent company contracts out their manufacturing. Many times these contractors will manufacture extra products in their plant in the 'off hours' and sell these items as if it were created by the parent company. Because the processes and materials are identical, it is nearly impossible to identify these objects as counterfeit from scrutinizing them because they are physically the same. In this case the primary difference is that the original manufacturing company was not the original owner who would receive the sales revenue from the object.

Consistent with the present disclosure, generating records of a tangible object in blockchain allows for a unique, and non-replicable, physical tag to be attached to any tangible object. Using a decentralized platform, a user may register as the owner and/or manufacturer of the object. When the owner is ready to sell the item, ownership may be transferred using a decentralized platform. All of these ownership transactions are stored as an immutable record that allows for the authentication of the original manufacturer, and the object's provenance.

Because the unique physical tags have a ledger of ownership, a buyer interested in purchasing a second-hand item can be certain that the seller owns the item. Furthermore, the object's provenance will allow the buyer to confirm that the claimed manufacturer was the original owner of the object to determine that it is an authentic item. The unique physical tags include non-counterfeitable, unique, readable patterns. The identity of each unique physical tag, and the associated object, are stored in a decentralized, and immutable record using a decentralized platform such as the Ethereum blockchain technology. Using the blockchain technology, the object's provenance, including the original manufacturer may be authenticated, current and past owners may be identified, and royalty requirements may be fulfilled during ownership transitions.

Generating records of a tangible object in blockchain, consistent with the present disclosure, allows for association of a unique physical tag to a tangible object. As described more thoroughly herein, an example method of the present disclosure begins with creation of a unique, non-replicable, physical tag that can be attached to a tangible object using different methods that include, but are not limited to a very high-bond adhesive, punch tag or other methods for attaching one object to another. In some examples, the unique physical tag may be embedded within the tangible object, or otherwise incorporated into a portion of the tangible object or part of the object manufacturing process itself. After attaching the unique physical tag to the tangible object, an owner can create an immutable blockchain record of the tangible object and the object's owner.

Buying or selling an item that has a unique and non-replicable physical tag provides greater peace of mind for the buyer and seller. The seller may set the 'status' of the object as 'Open For Transfer' meaning that the owner is interested in selling the tangible object. This can be proof for a buyer to see that the tangible object is available for sale and who the current owner is. When the seller/owner finds a buyer, a smart contract may be created between the authenticated owner and buyer. Using a blockchain platform, as described further herein, the buyer may place the agreed upon amount of Cryptocurrency/money into an escrow account. The seller/owner may change the status to 'Transfer Ownership To X' where X is the buyer's account. When the buyer receives the object, the buyer will read the physical tag to initiate the transfer of cryptocurrency to the seller. Responsive to the transfer of ownership, the ownership of the object is then automatically transferred to the stated buyer and stored in the decentralized application and the cryptocurrency in the escrow account is automatically transferred to the seller's account.

Turning now to the figures, FIG. 1 illustrates an example block diagram of a computing device including instructions to generate records of a tangible object in a blockchain, consistent with the present disclosure. As illustrated in FIG. 1, the computing device 100 may include a processor 102, and a computer-readable storage medium 104.

The processor 102 may be a central processing unit (CPU), a semiconductor-based microprocessor, and/or other hardware device suitable to control operations of the computing device 100. Computer-readable storage medium 104 may be an electronic, magnetic, optical, or other physical storage device that contains or stores executable instructions. Thus, computer-readable storage medium 104 may be, for example, Random Access Memory (RAM), an Electrically Erasable Programmable Read-Only Memory (EEPROM), a storage device, an optical disc, etc. In some examples, the computer-readable storage medium may be a non-transitory storage medium, where the term 'non-transitory' does not encompass transitory propagating signals. As described in detail below, the computer-readable storage medium 104 may be encoded with a series of executable instructions 106-108.

As illustrated, the computer-readable storage medium 104 may store instructions 106 that, when executed, cause a computing device to associate a unique physical tag with a tag identifier. As used herein, a unique physical tag refers to or includes a physical badge that is generated using one or more chaotic processes which make the physical badge difficult, if not impossible, to recreate. In various examples, the unique physical tag includes a substrate having a plurality of optically readable indicia disposed at random positions and having a fixed positional relationship within the substrate. As a non-limiting example, the unique physical tag includes a three-dimensional material with a plurality of randomly disposed items disposed therein. In various examples, the unique physical tags are generated with one or more chaotic processes that make it nearly impossible to replicate and/or counterfeit. The physical tag may also be a digital medium in which a random pattern is created or a random sequence of codes are created over time.

Every unique physical tag includes a unique, unreproducible, readable pattern, and each unique physical tag is associated with a tangible object using blockchain to maintain an immutable ledger. As a non-limiting example, a unique physical tag includes bubbles generated in a polymer during a reaction or an arrangement of fibers in a fabric. As another example, the unique tag can be a randomly generated radio frequency pattern or a sequence of pseudorandom numerical values over time. The pattern of bubbles and/or orientation of fibers generate a type of a 'fingerprint' or a unique pattern incapable of replication that can be converted into a unique code. Each unique physical tag may be associated with a tag identifier, such that the unique physical tag may be incorporated in a blockchain platform. As used herein, a tag identifier refers to or includes an alphanumeric value associated with the unique physical tag, and used to identify the unique physical tag in the blockchain platform.

The computer-readable storage medium 104 may store instructions 108 that, when executed, cause the computing device to associate the tangible object with the unique physical tag including the tag identifier, by generating a record of the tangible object as a block in a blockchain uniquely associated with the tag identifier. In various examples, the blockchain is managed by one or more devices on a decentralized network. Because the blockchain technology is decentralized it is nearly impossible to modify the records and a user can confirm the records independently.

In various examples, the unique physical tag is physically attached to a tangible object such as to an art piece, a handbag or even embedded in collector cards. Using blockchain technology, the unique physical tag may be associated with the tangible object and the ownership of the tangible object may be established. For instance, a block may be generated in the blockchain, identifying the owner of the tangible object.

Just as ownership may be recorded in blockchain using the unique physical tag, ownership may be transferred using blockchain. As an illustration, when the owner of the tangible object wishes to sell the object, the owner may provide the unique physical tag to a buyer, and the buyer may verify the identity of the associated object. The buyer may also verify the address of the owner and the object's transfer state. As used herein, a transfer state refers to or includes a type of possession associated with the tangible object at a particular point in time. Non-limiting examples of a transfer state which may be applied to an object in blockchain include 'Closed', 'InTransfer', and 'OpenToTransfer'.

The authenticity of the ownership state of the tangible object may be verified using blockchain. For instance, if the address of the owner does not match the address of the seller, then a buyer may conclude that the seller of the object is not the owner. Moreover, because ownership is recorded as a block in a blockchain, the history of ownership (e.g., ownership chain) may be verified using the blockchain ledger, as a user may also view the ownership ledger and dates of transfer. Yet further, the authenticity of the tangible object may also be verified using blockchain. For instance, if the tangible object is alleged to be manufactured by Manufacturer A, and the original owner (e.g., the first block in the block chain) does not correspond with Manufacturer A, then the buyer may question the authenticity of the tangible object. Conversely, if the tangible object is alleged to be manufactured by Manufacturer A, and the original owner (e.g., the first block in the block chain) corresponds with Manufacturer A, then the buyer may verify that the tangible object was legitimately manufactured by Manufacturer A.

The ownership of the unique physical tag and the associated tangible object may be maintained in a decentralized blockchain database. This database maintains an immutable record of who currently owns the unique physical tag and the associated item and who has previously owned the unique physical tag. By using a decentralized system, the blockchain platform remains as an effective source of validating authenticity of an object even if a manufacturer goes out of business or is otherwise obsolete.

In some examples, the computer-readable storage medium 104 may store instructions that, when executed, cause the computing device 100 to, in response to a request to transfer ownership of the tangible object, create on the blockchain, a smart contract specifying terms for transferring ownership of the tangible object. As used herein, a smart contract refers to or includes a computer program or a transaction protocol which is intended to automatically execute, control or document legally relevant events and actions according to the terms of a contract or an agreement. With the implementation of Cryptocurrency, based on blockchains, a "smart contract" may refer to or include a general purpose computation that takes place on a blockchain or distributed ledger. The US National Institute of Standards and Technology describes a "smart contract" as a "collection of code and data (sometimes referred to as functions and state) that is deployed using cryptographically signed transactions on the blockchain network".

Smart contracts provide a safe and transparent way of transferring the ownership of the object and funds from one person to another. A smart contract also provides a 'future proof' method for some of the technologies such as transfer of royalties. Because these contracts are in the blockchain, the royalties will continue to be paid and the ownership data will still continue even if the manufacturer of the unique physical tag and/or the manufacturer of the tangible object no longer exists.

In some examples, the computer-readable storage medium 104 may store instructions that, when executed, cause the computing device 100 to process the unique physical tag and use the tag identifier associated with the unique physical tag, display on a user interface, information about the associated object. Information about the associated object may include, but is not limited to an ownership ledger for the tangible object. In various examples, the ownership ledger may include a date and source of manufacture of the tangible object and a chain of ownership from the date of manufacture of the tangible object.

In some examples, the computer-readable storage medium 104 may store instructions that, when executed, cause the computing device 100 to process the unique physical tag. As used herein, to process the unique physical tag refers to or includes capturing a two-dimensional image of the unique physical tag, capturing a three-dimensional image of the unique physical tag, and/or capturing information on the unique physical tag using radio frequency identification (RFID), near-field communication, and other communication protocols. In response to processing the unique physical tag, the computing device may locate the tag identifier associated with the unique physical tag, and display on a user interface, information about the associated object. Put another way, the computing device 100 may process a unique physical tag (such as by capturing an image, RFID, or other unique physical tag), deterministically convert the captured unique physical tag to a numeric code (such as through a hash function), and use the numeric code to query the blockchain to identify information concerning the item. The identified information may be displayed on a user interface of the computing device 100.

In some examples, the computer-readable storage medium 104 may store instructions that, when executed, cause the computing device 100 to add a block to the blockchain indicating that the unique physical tag is damaged, invalid, or lost, and associate the tangible object with a second unique physical tag. In such examples, the second unique physical tag includes a second tag identifier and is generated to include a record of the tangible object as a block in the blockchain that is uniquely associated with the second tag identifier.

In some examples, a plurality of unique physical tags may be placed on or in a tangible object. For instance, one unique physical tag may be placed on the packaging which allows the buyer to confirm that the product was manufactured by a particular company before purchasing the product. A second unique physical tag may be affixed to the product inside the packaging. At the time of manufacturing, the status of the tangible object may be set to 'Open'. When the consumer purchases the product, the consumer may scan the unique physical tag, such as with a mobile application, and set the status to 'Accept Ownership'. Responsive to selecting 'Accept Ownership' for the tangible object, the consumer is registered as the owner of the tangible object and a new block may be generated in the blockchain, recording the consumer (e.g., new owner) as the owner of the tangible object. The 'outer' tag and the 'inner' tag can be associated in the decentralized application such that by scanning the 'outer' tag the buyer can confirm that the status of the 'inner' tag is set to 'Open' and not assigned to someone else furthermore, the buyer can confirm that the original owner is the expected manufacturer to ensure that the item is authentic.

In various examples, unique physical tags may be associated with prescription medications, medical assays, and other healthcare articles, thereby serving as a method of verifying the authenticity of such healthcare articles. For instance, for prescription medications, consumers rely on the trust of their pharmacist to use authentic medication when filling a prescription. Using a CountBase feature in the unique physical tag technology, a user may ensure that the medication is authentic. As used herein, a CountBase feature refers to or includes a system in which a plurality of items in a same package inherit the same first block in a blockchain such that each of the plurality of items may be verified.

As an illustration, the CountBase feature may be used to track a plurality of lots of pills shipped to a pharmacy. In this example, the original CountBase item (a shipment of pills) would have N sub-objects (individual pills in the shipment). Let us assume that the company 'MedInc' produces products that are sent to pharmacies in bottles containing 1000 pills. When the pharmacist puts pills into a particular bottle for a customer, the bottle may include a unique physical tag on it and the pharmacist will transfer, say 100 pills to that object. The CountBase feature may then remove 100 pills from the 'source' bottle and create a new 'object' with 100 pills. The ownership chain may then be inherited by the current bottle. The patient can scan their bottle and confirm that the original owner was MedInc.

With medications, there might be an 'end user' status, meaning that the item cannot be transferred to someone else and for privacy reasons one may not want to reveal the current owner. However, for other items that have multiple subparts, the current owner may again split their lot into multiple lots and the inheritance would continue.

As a further example of the CountBase feature, the tangible object may include a plurality of vaccines, such as a plurality of doses of a vaccine for severe acute respiratory syndrome coronavirus 2 (SARS-CoV-2). In such examples, the medium 104 further includes instructions that when executed cause the computing device 100 associate the SARS-CoV-2 vaccine doses with the unique physical tag including the tag identifier, by generating a record of the SARS-CoV-2 vaccine doses as an element in the blockchain that is uniquely associated with the tag identifier, including a date, time, lot number, and manufacturer of the SARS-CoV-2 vaccine doses.

As another example of the CountBase feature, the tangible object may include a plurality of doses of a therapeutic. For instance, the tangible object may include a plurality of doses of a therapeutic for SARS-CoV-2. In such an example, the medium 104 further includes instructions that when executed cause the computing device to associate the SARS-CoV-2 therapeutic doses with the unique physical tag including the tag identifier, by generating a record of the SARS-CoV-2 therapeutic doses as a block in the blockchain uniquely associated with the tag identifier, including a date, time, lot number, and manufacturer of the SARS-CoV-2 therapeutic doses.

As yet another example, the tangible object may include a plurality of antibody assays for SARS-CoV-2. In such examples, the medium 104 includes instructions that when executed cause the computing device 100 to associate the SARS-CoV-2 antibody assays with the unique physical tag including the tag identifier, by generating a record of the SARS-CoV-2 antibody assays as a block in the blockchain uniquely associated with the tag identifier, including a date, time, lot number, and manufacturer of the SARS-CoV-2 antibody assays.

Although examples herein describe a vaccine, therapeutic, and/or antibody assay for SARS-CoV-2, the present disclosure is not limited to such applications. The unique physical tags and associated ownership ledger may be used to track ownership of healthcare articles for any healthcare application. In some examples, the tangible object may include a plurality of vaccines, therapeutics, or assays for diagnosis or treatment of a human or animal subject. In such examples, the medium 104 includes instructions that when executed cause the computing device 100 to associate the vaccines, therapeutics, or assays with the unique physical tag including the tag identifier, by generating a record of the vaccines, therapeutics, or assays as a block in the blockchain uniquely associated with the tag identifier. The record in the blockchain may include, but is not limited to, a date, time, lot number, and manufacturer of the vaccines, therapeutics, or assays. For each sub-lot of the plurality of vaccines, therapeutics, or assays, a unique physical tag including a tag identifier may be associated with the sub-lot, by generating a record of the sub-lot as a block in a blockchain uniquely associated with the tag identifier.

Figure 2:
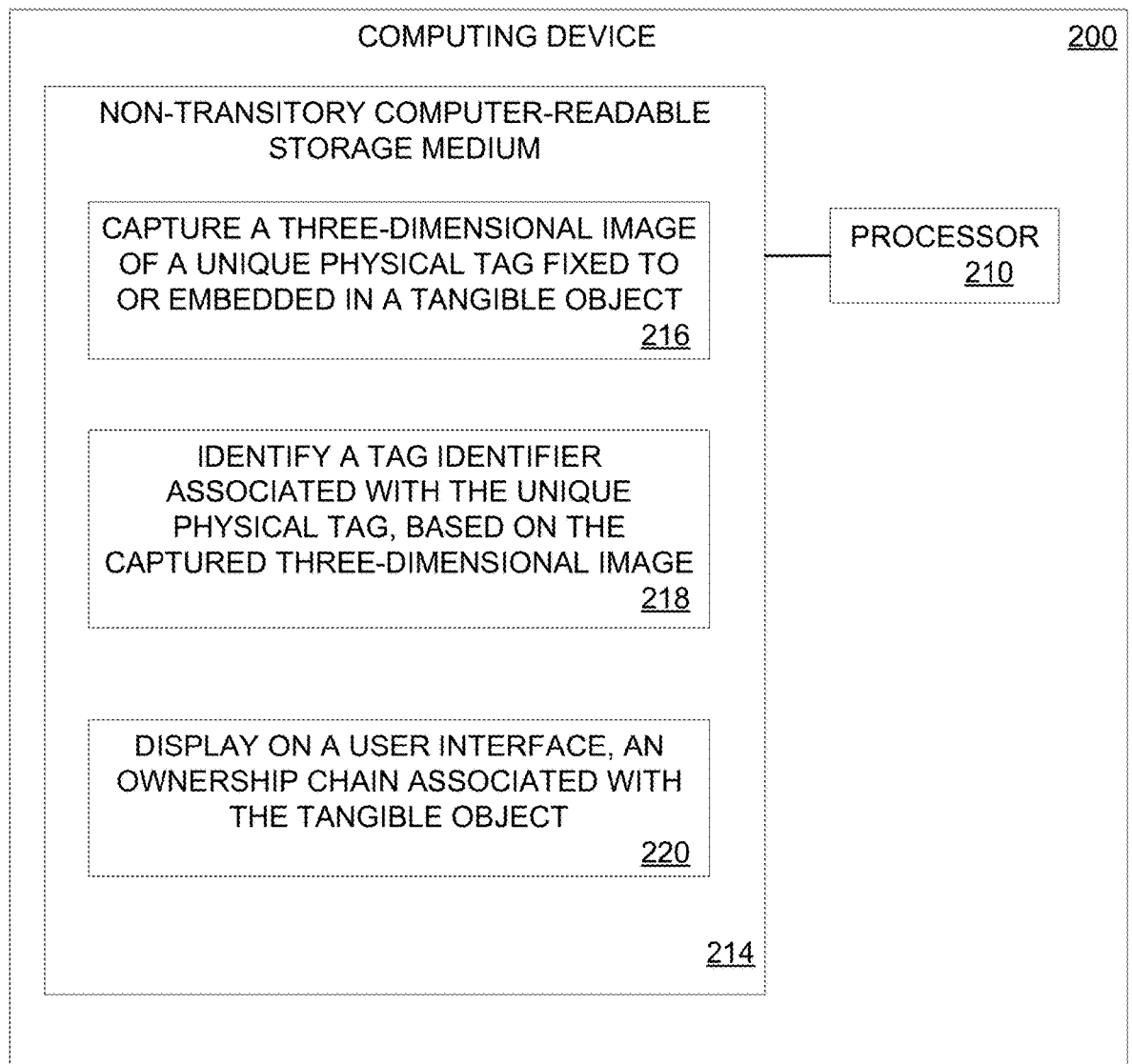
FIG. 2 illustrates an example block diagram of a computing device including instructions to generate records of a tangible object in blockchain, consistent with the present disclosure.

FIG. 2 illustrates an example block diagram of a computing device 200 including instructions to generate records of a tangible object in blockchain, consistent with the present disclosure. As illustrated in FIG. 2, the computing device 200 may include a processor 210, and a computer-readable storage medium 214. The computing device 200 may be the same as, or different than, the computing device 100 illustrated in FIG. 1. Similarly, the processor 210 may be the same as or different than the processor 102, and the computer-readable medium 104 may be the same as or different than the computer-readable medium 214.

The processor 210 may be a CPU, a semiconductor-based microprocessor, and/or other hardware device suitable to control operations of the computing device 200. Computer-readable storage medium 214 may be an electronic, magnetic, optical, or other physical storage device that contains or stores executable instructions. Thus, computer-readable storage medium 214 may be, for example, RAM, an EEPROM, a storage device, an optical disc, etc. In some examples, the computer-readable storage medium may be a non-transitory storage medium, where the term 'non-transitory' does not encompass transitory propagating signals. As described in detail below, the computer-readable storage medium 214 may be encoded with a series of executable instructions 216-220.

As illustrated, the computer-readable storage medium 214 may store instructions 216 that, when executed, cause the computing device 200 to capture a three-dimensional image of a unique physical tag fixed to or embedded in a tangible object. As described herein, the unique physical tag may in some examples include a three-dimensional substrate having a plurality of optically readable indicia disposed at random positions and having a fixed positional relationship within the three-dimensional substrate. The three-dimensional image may capture the positional relationship of each optically readable indicia within the substrate.

The computer-readable storage medium 214 may store instructions 218 that, when executed, cause the computing device 200 to identify a tag identifier associated with the unique physical tag, based on the captured three-dimensional image. As described herein, the ownership of the unique physical tag and the associated tangible object may be maintained in a decentralized blockchain database. Each tag is also associated with a tag identifier, which may be used to identify the blockchain associated with the tangible object. By processing the unique physical tag with an appropriate endpoint device (such as a smartphone or portable computing device with image capture capabilities), the tag identifier may be identified in the blockchain database.

The computer-readable storage medium 214 may store instructions 220 that, when executed, cause the computing device to display on a user interface, an ownership chain associated with the tangible object and stored in a blockchain uniquely associated with the tag identifier.

In some examples, computer-readable storage medium 214 may store instructions that, when executed, cause the computing device 200 to receive input identifying a user of the computing device as a current owner of the tangible object. The computing device 200 may verify the user as the current owner of the tangible object as indicated in the blockchain, and responsive to input from the user to transfer ownership of the tangible object, the computing device 200 may change a status of the tangible object in the blockchain indicating that the tangible object is open for transfer.

Figure 3:
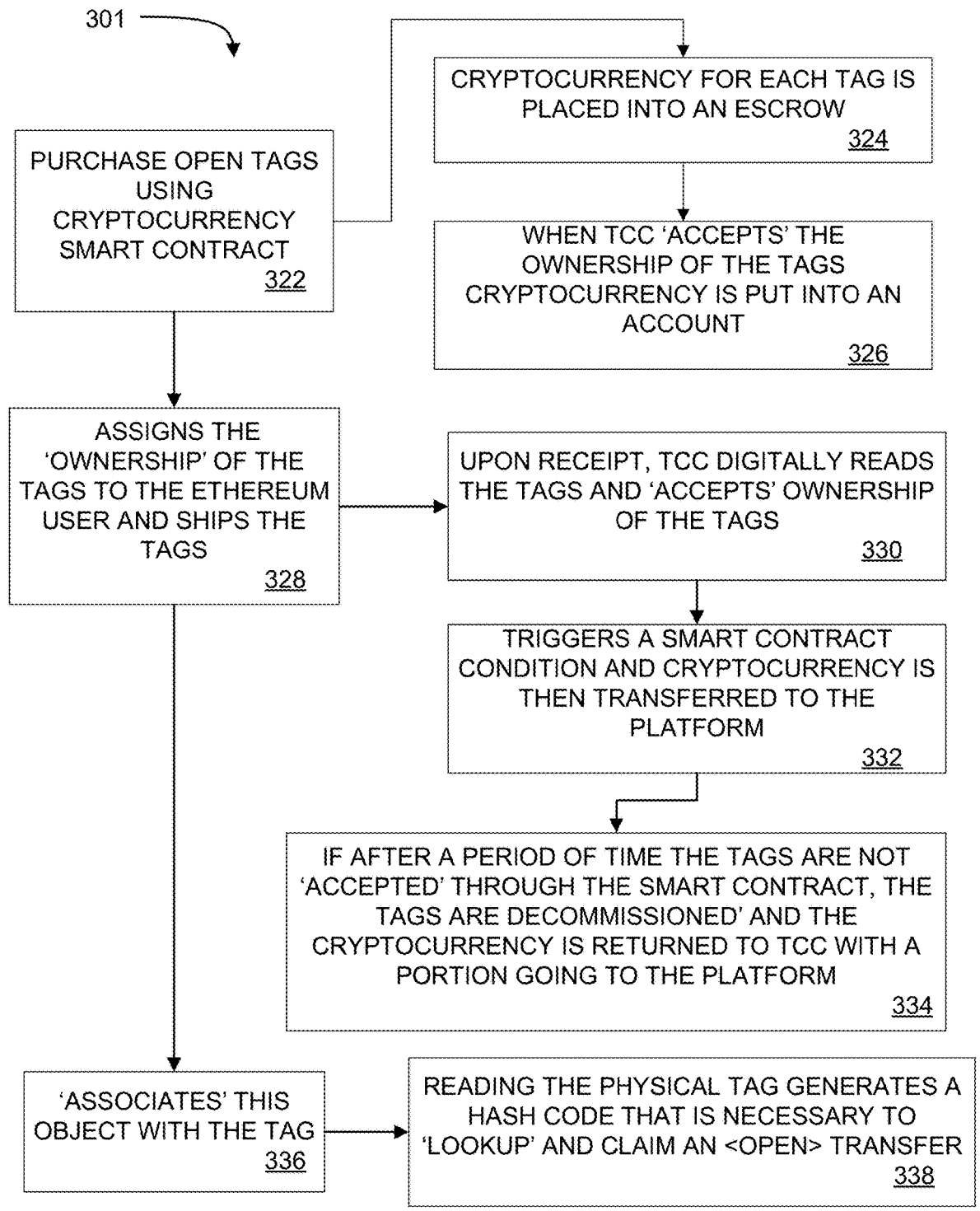
FIG. 3 illustrates a flow chart of an example method for generating records of a tangible object in blockchain, consistent with the present disclosure. Particularly.

FIG. 3 illustrates a flow chart of an example method 301 for generating records of a tangible object in blockchain, consistent with the present disclosure. Particularly, FIG. 3 illustrates an example transaction between a platform operator and a trading card company (TCC). As used herein, the platform operator refers to or includes an entity that sells unique physical tags and associates a blockchain with the unique physical tag, as illustrated and described with regards to FIG. 1 and FIG. 2.

At 322, the method begins with the trading card company purchasing open tags using a Cryptocurrency smart contract, from the platform operator. As used herein, a 'tag' refers to a unique physical tag. As described with reference to FIG. 1, a tag (e.g., unique physical tag) may have a status, allowing buyers to identify the tag or associated item as available for sale. In the example illustrated in FIG. 3, unique physical tags may be purchased at 322. The Cryptocurrency for each unique physical tag is placed into an escrow at 324, and when the trading card company accepts ownership of the unique physical tags, the Cryptocurrency is placed into an account of the platform operator at 326.

At 328, the platform operator assigns the ownership of the unique physical tags to the Cryptocurrency user, and ships the unique physical tags to the trading card company. Upon receipt of the purchased unique physical tags, the trading card company digitally reads the tags (e.g., processes the tags) and accept ownership of the tags at 330 (as described with regards to FIG. 1 and FIG. 2).

Responsive to the trading card company accepting ownership of the tags, a smart contract condition is triggered (e.g., the acceptance of the tags), and Cryptocurrency is transferred to the platform operator at 332. However, if after a period of time the tags are not accepted through the smart contract, then the tags could be decommissioned (e.g., labeled as inactive and unavailable for purchase or transfer) and the Cryptocurrency is returned to the trading card company with a portion going to the platform operator at 334.

At 336, the trading card company associates a tangible object with each respective tag purchased. Once the tangible object is associated with the respective tag, reading the unique physical tag generates a hash code that is necessary to perform a lookup to identify the tag identifier and claim an open transfer. As discussed herein, each unique physical tag may have a status, and those with an open status may be transferred between parties.

Figure 4:
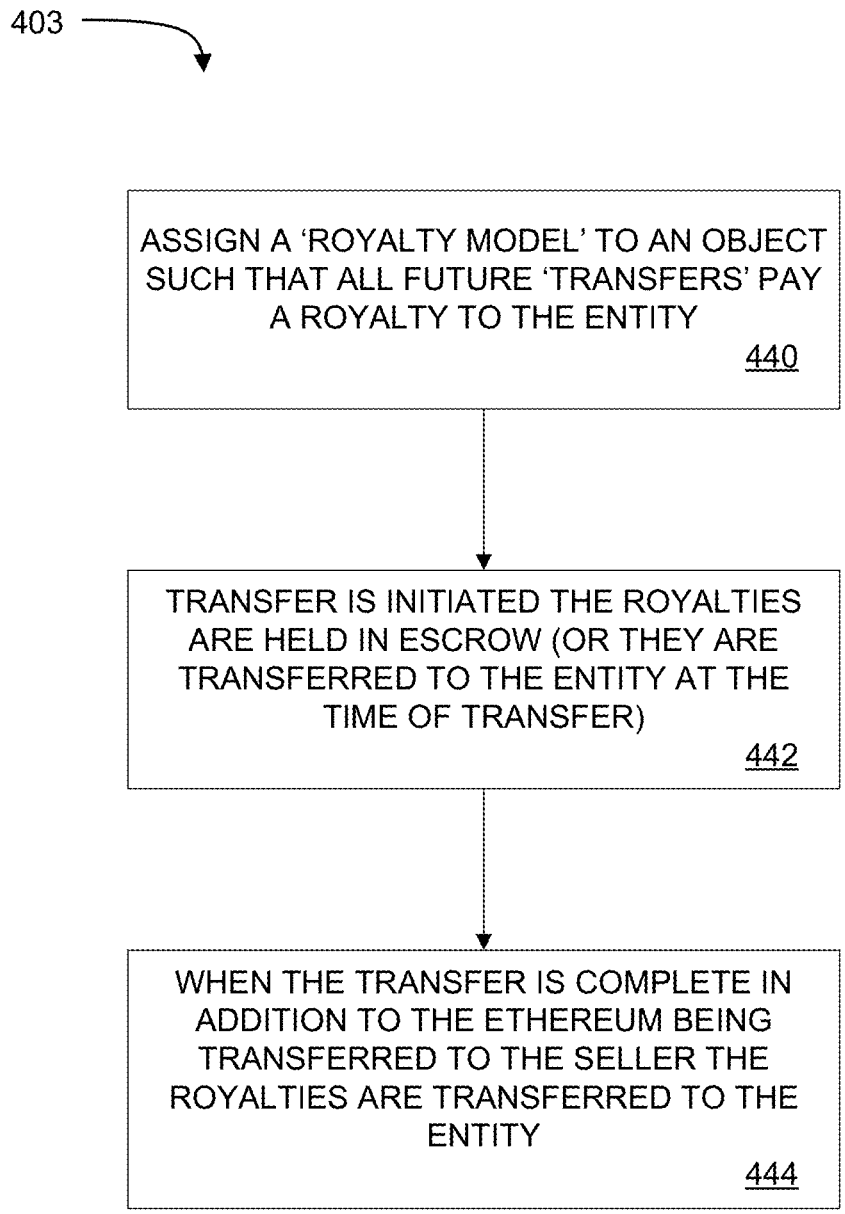
FIG. 4 illustrates a flow chart of an example method for generating records of a tangible object in blockchain, consistent with the present disclosure. More particularly.

FIG. 4 illustrates a flow chart of an example method 403 for generating records of a tangible object in blockchain, consistent with the present disclosure. More particularly, FIG. 4 illustrates an example method of assigning and paying royalties using blockchain, as described herein.

At 440, the method 403 includes assigning a royalty model to an object such that all future transfers pay a royalty to the artist. For instance, as described herein, a smart contract may be created at a time of a transfer of a tangible object using blockchain. The smart contract may specify a particular royalty rate that is to be paid to a party, such as an artist and/or an originator of the tangible object when one or more future transactions are executed. For the subsequent transfers of ownership of the tangible object, a new block is created in the blockchain, with the royalty rate carried through in the smart contract of each transaction.

At 442, when a transfer is initiated in which ownership of a tangible object is transferred from one entity or person to another entity or person, the royalties associated with the royalty rates are held in escrow or transferred to the parties (or party) at the time of transfer. Upon completion of the transfer, cryptocurrency is transferred to the seller and royalties are transferred to the entity (e.g., artist, originator, etc.) pursuant to the royalty model at 444.

Figure 5:
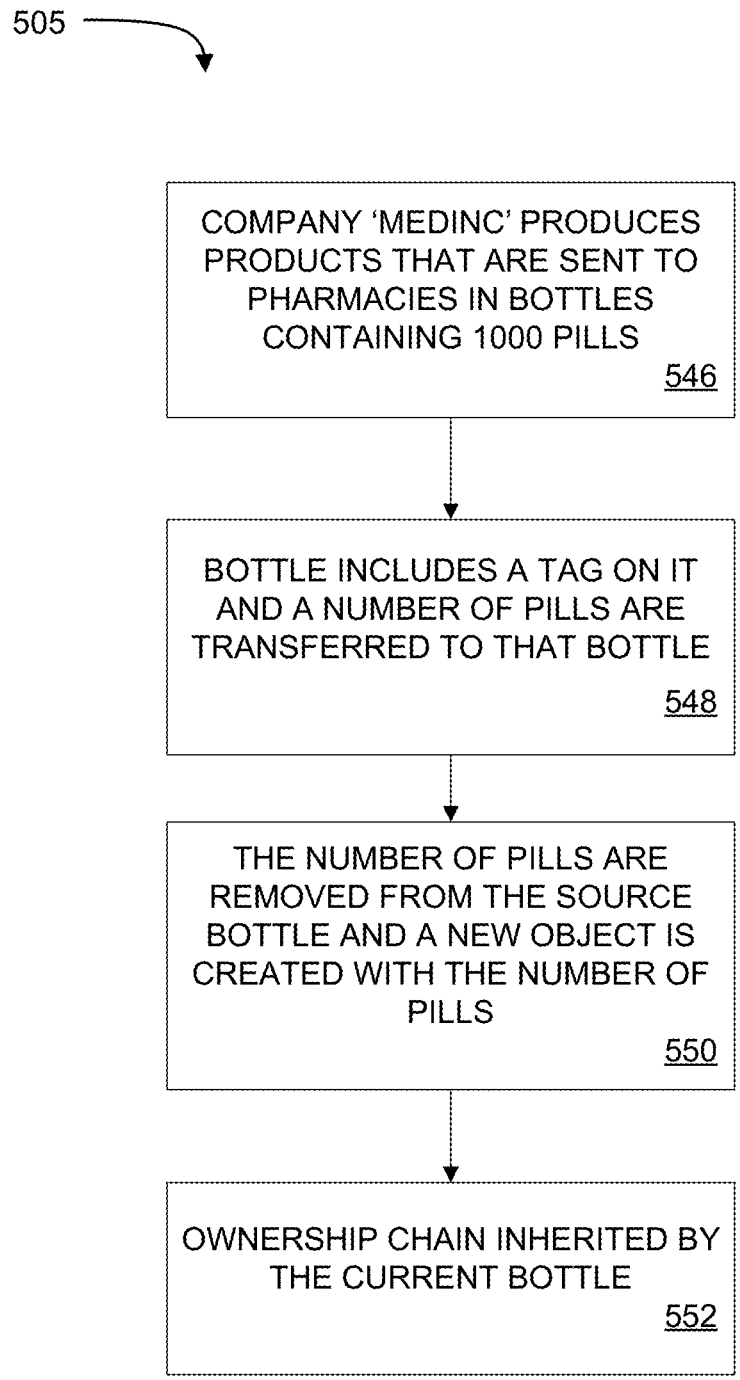
FIG. 5 illustrates a flow chart of an example method for generating records of a tangible object in blockchain, consistent with the present disclosure. Particularly.

FIG. 5 illustrates a flow chart of an example method 505 for generating records of a tangible object in blockchain, consistent with the present disclosure. Particularly, FIG. 5 illustrates an example method of a CountBase feature, consistent with the present disclosure.

As illustrated in FIG. 5, the method 505 begins at 546 where a company produces a product that is to be distributed in subparts. For instance, example company 'MedInc' produces products that are sent to pharmacies in bottles containing 1000 pills. Each bottle including 1000 pills (or other example volume) includes a unique physical tag and associated blockchain, as described herein. When dispensing the medication (e.g., pills) into a particular bottle for a customer, the particular bottle for the customer may also include a unique physical tag on it and the pharmacist may transfer a number of pills (such as 100 pills) to the particular bottle for the customer at 548. The number of pills are removed from the source bottle and a new object is created with the number of pills for the particular bottle for the customer at 550. That is, a new block for a blockchain associated with the particular bottle for the customer is created at 550.

Under the CountBase feature, all subparts stemming from a same source object inherit the ownership chain of the source object. Continuing with the pill example, the ownership chain of the source bottle of pills may be inherited by the particular bottle for the customer at 552. As such, each patient that receives a bottle of pills originating from the source bottle, may scan their respective bottle and confirm that the original owner was MedInc.

With medications, there might be an 'end user' status, meaning that the item cannot be transferred to someone else and for privacy reasons one may not want to reveal the current owner. However, for other items that have multiple subparts, the current owner may again split their lot into multiple lots and the inheritance would continue.

As a further example of the CountBase feature, the tangible object may include a plurality of vaccines, such as a plurality of doses of a vaccine for severe acute respiratory syndrome coronavirus 2 (SARS-CoV-2). In such examples, the medium 104 further includes instructions that when executed cause the computing device 100 associate the SARS-CoV-2 vaccine doses with the unique physical tag including the tag identifier, by generating a record of the SARS-CoV-2 vaccine doses as a block in the blockchain uniquely associated with the tag identifier, including a date, time, lot number, and manufacturer of the SARS-CoV-2 vaccine doses.

As another example of the CountBase feature, the tangible object may include a plurality of doses of a therapeutic. For instance, the tangible object may include a plurality of doses of a therapeutic for SARS-CoV-2. In such an example, the medium 104 further includes instructions that when executed cause the computing device to associate the SARS-CoV-2 therapeutic doses with the unique physical tag including the tag identifier, by generating a record of the SARS-CoV-2 therapeutic doses as a block in the blockchain uniquely associated with the tag identifier, including a date, time, lot number, and manufacturer of the SARS-CoV-2 therapeutic doses.

As yet another example, the tangible object may include a plurality of antibody assays for SARS-CoV-2. In such examples, the medium 104 includes instructions that when executed cause the computing device 100 to associate the SARS-CoV-2 antibody assays with the unique physical tag including the tag identifier, by generating a record of the SARS-CoV-2 antibody assays as a block in the blockchain uniquely associated with the tag identifier, including a date, time, lot number, and manufacturer of the SARS-CoV-2 antibody assays.

Although examples herein describe a vaccine, therapeutic, and/or antibody assay for SARS-CoV-2, the present disclosure is not limited to such applications. The unique physical tags and associated ownership ledger may be used to track ownership of healthcare articles for any healthcare application. In some examples, the tangible object may include a plurality of vaccines, therapeutics, or assays for diagnosis or treatment of a human or animal subject. In such examples, the medium 104 includes instructions that when executed cause the computing device 100 to associate the vaccines, therapeutics, or assays with the unique physical tag including the tag identifier, by generating a record of the vaccines, therapeutics, or assays as a block in the blockchain uniquely associated with the tag identifier. The record in the blockchain may include, but is not limited to, a date, time, lot number, and manufacturer of the vaccines, therapeutics, or assays. For each sub-lot of the plurality of vaccines, therapeutics, or assays, a unique physical tag including a tag identifier may be associated with the sub-lot, by generating a record of the sub-lot as a block in a blockchain uniquely associated with the tag identifier.

Figure 6:
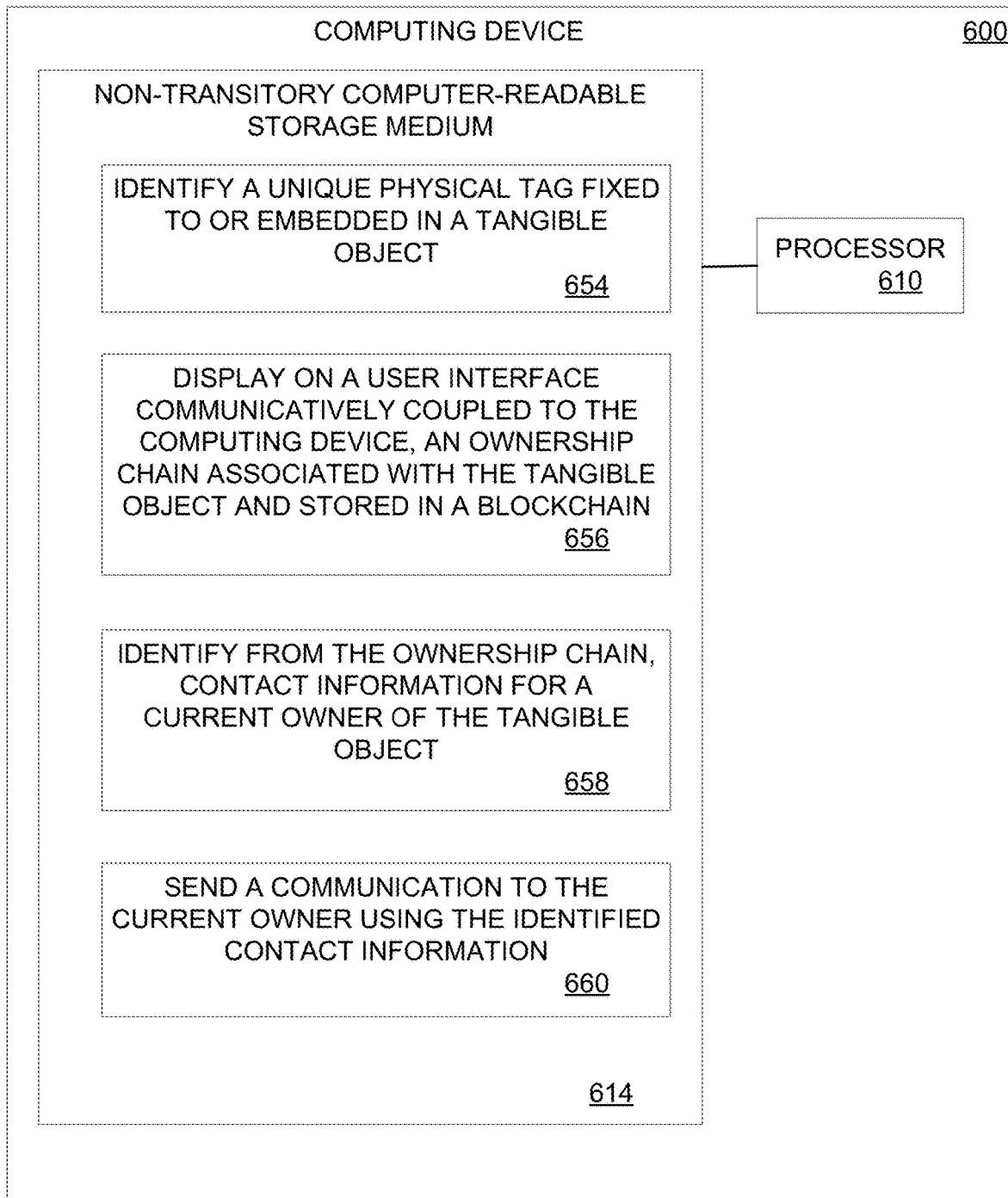
FIG. 6 illustrates a block diagram of an example computing device including instructions to generate records of a tangible object in blockchain, consistent with the present disclosure. More particularly.
Figure 7:
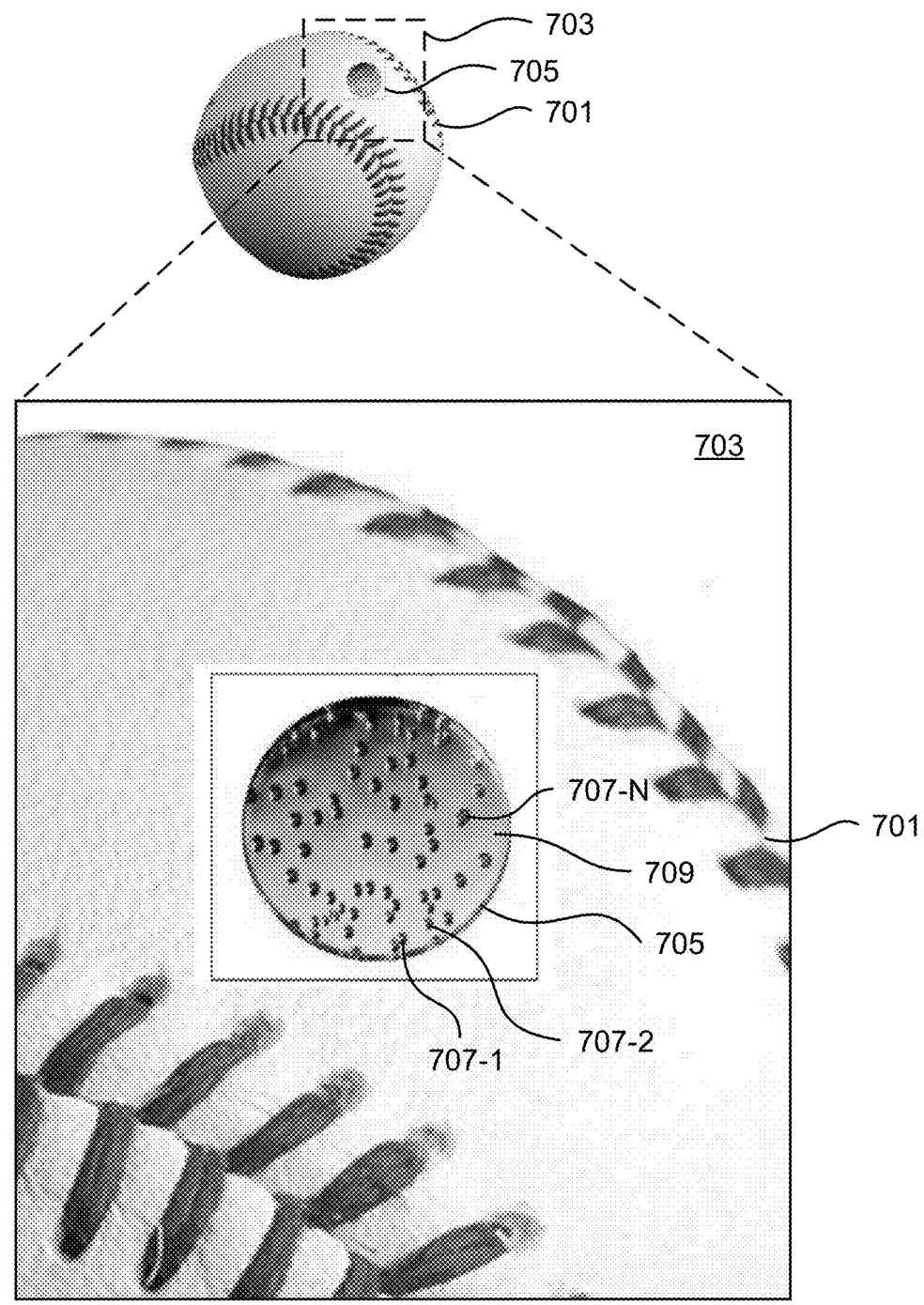
FIG. 7 illustrates an example an example tangible object 701 with a unique physical tag 705, consistent with the present disclosure. Particularly.

FIG. 6 illustrates a block diagram of an example computing device 600 including instructions to generate records of a tangible object in blockchain, consistent with the present disclosure. More particularly, FIG. 6 illustrates an example computing device 600 for identifying ownership of an item using the blockchain method described herein. In various examples, the unique physical tag and associated blockchain may be used to identify an owner of a lost item. As illustrated in FIG. 6, the computing device 600 may include a processor 610, and a computer-readable storage medium 614. The computing device 600 may be the same as, or different than, the computing device 100 illustrated in FIG. 1. Similarly, the processor 610 may be the same as or different than the processor 102, and the computer-readable medium 614 may be the same as or different than the computer-readable medium 104.

The processor 610 may be a CPU, a semiconductor-based microprocessor, and/or other hardware device suitable to control operations of the computing device 600. Computer-readable storage medium 614 may be an electronic, magnetic, optical, or other physical storage device that contains or stores executable instructions. Thus, computer-readable storage medium 614 may be, for example, RAM, an EEPROM, a storage device, an optical disc, etc. In some examples, the computer-readable storage medium may be a non-transitory storage medium, where the term 'non-transitory' does not encompass transitory propagating signals. As described in detail below, the computer-readable storage medium 614 may be encoded with a series of executable instructions 654-660.

As illustrated in FIG. 6, computer-readable storage medium 614 may store instructions 654 that, when executed, cause computing device 600 to identify a unique physical tag fixed to or embedded in a tangible object. For instance, computing device 600 may process the unique physical tag, such as by capturing an image of the unique physical tag, by RFID, NFC, or other identification means.

Computer-readable storage medium 614 may store instructions 656 that, when executed, cause computing device 600 to display on a user interface communicatively coupled to the computing device, an ownership chain associated with the tangible object and stored in a blockchain. In some examples, computing device 600 may be a portable computing device such as a mobile phone, tablet computer, or notebook computer among other non-limiting examples. As described herein, once the unique physical tag is processed, a hash code is generated that is necessary to perform a lookup to identify the tag identifier and blockchain associated with the unique physical tag. Responsive to identification of the blockchain associated with the unique physical tag, the ownership chain recorded in the blockchain may be displayed on a user interface of the computing device 600 or communicatively coupled to the computing device 600.

Computer-readable storage medium 614 may store instructions 658 that, when executed, cause computing device 600 to identify from the ownership chain, contact information for a current owner of the tangible object. For instance, a name, phone number, mailing address, email address, and/or other contact information may be provided for the owner of the tangible object and previous owners in the ownership chain. In some examples, the computing device 600 may provide an option to directly contact the current owner of the tangible object. For instance, the ability to create new blockchains and associate them with tangible objects as described herein, may be provided by a blockchain platform. A platform operator refers to or includes a company that hosts the blockchain platform and makes it available for public and/or private use. The platform operator may provide to users, an application which may be operable on mobile computing devices, which allows users to access the blockchain platform on their mobile computing devices. Using this blockchain platform, a user may scan unique physical tags, identify ownership of a tangible object, transfer ownership of tangible objects, find tangible objects that are open for transfer (e.g., sale), identify a number of similar tangible objects on the blockchain platform (e.g., determine how 'rare' the object is), and transfer royalties to an entity, among other non-limiting functions. The blockchain platform may also allow users to, through the blockchain platform, identify and contact an owner of a tangible object that may be lost.

Although specific examples have been illustrated and described herein, a variety of alternate and/or equivalent implementations may be substituted for the specific examples shown and described without departing from the scope of the present disclosure. This application is intended to cover any adaptations or variations of the specific examples discussed herein. Therefore, it is intended that this disclosure be limited only by the claims and the equivalents thereof.

The invention claimed is:

1. A non-transitory computer-readable storage medium comprising instructions that when executed cause a computing device to:
   associate a unique physical tag with a tag identifier, wherein the unique physical tag includes a substrate having a plurality of optically readable indicia disposed at random positions and having a fixed positional relationship within the substrate; and
   associate the tangible object with the unique physical tag including the tag identifier, by generating a record of the tangible object as a block in a blockchain uniquely associated with the tag identifier, wherein the blockchain is managed by one or more devices on a decentralized network.

2. The medium of claim 1, including instructions that when executed cause the computing device to, in response to a request to transfer ownership of the tangible object, create on the blockchain, a smart contract specifying terms for transferring ownership of the tangible object.

3. The medium of claim 1, including instructions that when executed cause the computing device to process the unique physical tag and using the tag identifier associated with the unique physical tag, and display on a user interface, information about the associated object including an ownership ledger for the tangible object, wherein the ownership ledger includes a date and source of manufacture of the tangible object and a chain of ownership from the date of manufacture of the tangible object.

4. The medium of claim 1, including instructions that when executed cause the computing device to capture information on the unique physical tag using radio frequency identification (RFID), near-field communication, computer vision on a 2D and/or 3D tag, and/or by reading a sequence of pseudorandom numerical values over time from a device.

5. The medium of claim 1, including instructions that when executed cause the computing device to:
   add a block to the blockchain indicating that the unique physical tag is damaged or lost;
   associate the tangible object with a second unique physical tag including a second tag identifier by generating a record of the tangible object as a block in a second blockchain uniquely associated with the second tag identifier, wherein the second blockchain is managed by one or more devices on a decentralized network; and
   associate a ledger of ownership from the blockchain with a current record of ownership recorded in the second blockchain.

6. The medium of claim 1, wherein the tangible object is a plurality of vaccines, therapeutics, or antibody assays for severe acute respiratory syndrome coronavirus 2 (SARS-CoV-2), the medium further including instructions that when executed cause the computing device to:
   at a time of manufacture of the SARS-CoV-2 vaccines, therapeutics, or antibody assays, associate the SARS-CoV-2 vaccines, therapeutics, or antibody assays with the unique physical tag including the tag identifier, by generating a record of the SARS-CoV-2 vaccines, therapeutics, or antibody assays as a block in the blockchain uniquely associated with the tag identifier, including a date, time, lot number, and manufacturer of the SARS-CoV-2 vaccines, therapeutics, or antibody assays.

7. The medium of claim 1, wherein the tangible object is a plurality of vaccines, therapeutics, or assays for diagnosis or treatment of a human or animal subject, the medium further including instructions that when executed cause the computing device to:
   at a time of manufacture of the vaccines, therapeutics, or assays, associate the vaccines, therapeutics, or assays with the unique physical tag including the tag identifier, by generating a record of the vaccines, therapeutics, or assays as a block in the blockchain uniquely associated with the tag identifier, including, but not limited to a date, time, lot number, and manufacturer of the vaccines, therapeutics, or assays; and
   for each sub-lot of the plurality of vaccines, therapeutics, or assays, associate a unique physical tag including a tag identifier with the sub-lot, by generating a record of the sub-lot as a block in a blockchain uniquely associated with the tag identifier, wherein the blockchain of each respective sub-lot includes the date, time, lot number, and manufacturer of the lot.

8. The medium of claim 1, including instructions that when executed cause the computing device to:
   receive input identifying a user of the computing device as a current owner of the tangible object;
   verify the user as the current owner of the tangible object as indicated in the blockchain; and
   responsive to input from the user to transfer ownership of the tangible object, change a status of the tangible object in the blockchain indicating that the tangible object is open for transfer.

9. The medium of claim 1, including instructions that when executed cause the computing device to:
   responsive to a request from a user verified as the current owner of the tangible object as indicated in the blockchain, to transfer ownership of the tangible object, create a smart contract between the verified owner and the receiver, wherein the smart contract includes terms for transferring ownership of the tangible object from the verified owner to the receiver.

10. The medium of claim 9, including instructions that when executed cause the computing device to:
    change an ownership status of the tangible object in the ownership chain indicating a transfer of ownership to the receiver, in response to deposit of funds in an escrow account associated with the blockchain, wherein the deposit of funds fulfill at least one obligation of the smart contract.

11. The medium of claim 9, including instructions that when executed cause a computing device to:
    record the receiver as the current owner of the tangible object in the blockchain, in response to fulfillment of the terms of the smart contract.

12. The medium of claim 9, including instructions that when executed cause a computing device to:
    record, in the blockchain and in response to fulfillment of the terms of the smart contract, a date of transfer of ownership of the tangible object.

13. The medium of claim 1 including instructions that when executed cause the computing device to:
    responsive to a request from a user verified as the current owner of the tangible object as indicated in the blockchain, to transfer ownership of the tangible object, create a smart contract between the verified owner and a buyer, wherein the smart contract includes a royalties rate owed to a an entity creator of the tangible object upon the transfer of ownership of the tangible object; and responsive to the transfer of ownership of the tangible object from the owner to the buyer, deposit funds corresponding with the royalties rate in an escrow account for the entity.

14. The medium of claim 1, wherein the blockchain is managed by one or more devices on a decentralized network, the medium further including instructions that when executed cause the computing device to:
   identify from the blockchain, manufacturing information associated with the tangible object; and
   retrieve from a database managed by the one or more devices, information regarding a number of items similar to the tangible object that were manufactured at a same time as the tangible object.

15. A method, comprising:
   generating a unique physical tag, wherein the unique physical tag includes a three-dimensional substrate having a plurality of optically readable indicia disposed at random positions and having a fixed positional relationship within the three-dimensional substrate;
   embedding the unique physical tag in a tangible object;
   associating the tangible object with the unique physical tag, by generating a record of the tangible object as a block in a blockchain uniquely associated with the unique physical tag, wherein the blockchain is managed by one or more devices on a decentralized network; and
   recording a chain of ownership of the tangible object by recording in the blockchain, ownership of the tangible object from a point of manufacture.

16. The method of claim 15, wherein generating the unique physical tag includes generating bubbles in a polymer or arranging fibers in a fabric.

17. The method of claim 15, wherein recording the chain of ownership includes creating an immutable ledger of ownership in the blockchain.

18. The method of claim 15, wherein the unique physical tag is a second unique physical tag, the method including:
   generating a first unique physical tag, wherein the first unique physical tag includes a three-dimensional substrate having a plurality of optically readable indicia disposed at random positions and having a fixed positional relationship within the three-dimensional substrate;
   affixing the first unique physical tag to a package containing the tangible object; and
   embedding the second unique physical tag in the tangible object;
   wherein the first unique physical tag is associated with a record of the tangible object as a block in the blockchain and reflects ownership of the tangible object from a point of manufacture, and wherein the second unique physical tag has an open status that is claimable by a buyer of the tangible object.

* * * * *